(12) United States Patent
Rhodes et al.

(10) Patent No.: US 11,553,934 B2
(45) Date of Patent: Jan. 17, 2023

(54) CUSTOMIZED PATIENT-SPECIFIC ORTHOPAEDIC SURGICAL INSTRUMENTS

(71) Applicant: DEPUY SYNTHES PRODUCTS, INC., Raynham, MA (US)

(72) Inventors: James M. Rhodes, Warsaw, IN (US); Shawnoah S. Pollock, South Bend, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 223 days.

(21) Appl. No.: 17/115,067

(22) Filed: Dec. 8, 2020

(65) Prior Publication Data
US 2021/0085345 A1 Mar. 25, 2021

Related U.S. Application Data

(62) Division of application No. 15/992,059, filed on May 29, 2018, now Pat. No. 10,856,891.

(51) Int. Cl.
*A61B 17/17* (2006.01)
*A61B 17/15* (2006.01)
*A61B 17/16* (2006.01)
A61B 34/10 (2016.01)
A61B 17/56 (2006.01)
A61F 2/30 (2006.01)

(52) U.S. Cl.
CPC ........ *A61B 17/1764* (2013.01); *A61B 17/155* (2013.01); *A61B 17/1675* (2013.01); *A61B 17/157* (2013.01); *A61B 2017/568* (2013.01); *A61B 2034/105* (2016.02); *A61F 2/30942* (2013.01)

(58) Field of Classification Search
CPC ............. A61B 17/1764; A61B 17/155; A61B 17/1675; A61B 17/157; A61B 2017/568; A61B 2034/105
See application file for complete search history.

(56) References Cited

U.S. PATENT DOCUMENTS

| 8,157,867 B2* | 4/2012 | Goble | A61B 17/1764 623/20.15 |
|---|---|---|---|
| 8,668,700 B2* | 3/2014 | Catanzarite | A61B 17/1764 606/88 |
| 9,005,207 B2* | 4/2015 | Dodds | A61B 17/155 606/88 |
| 10,856,891 B2 | 12/2020 | Rhodes et al. | |
| 2012/0203233 A1* | 8/2012 | Yoshida | A61B 34/10 703/1 |

(Continued)

OTHER PUBLICATIONS

International Search Report, International Application No. PCT/IB2019/053679, dated Oct. 1, 2019, 6 pages.

*Primary Examiner* — Kevin T Truong
*Assistant Examiner* — Tracy L Kamikawa
(74) *Attorney, Agent, or Firm* — Barnes & Thornburg LLP (57) ABSTRACT

An orthopaedic surgical instrument is provided having a first customized patient-specific surgical instrument and a second customized patient-specific surgical instrument configured to be removably coupled to the first customized patient-specific surgical instrument. The second customized patient-specific surgical instrument includes a body positioned in a gap defined between posteriorly-extending arms of the first customized patient-specific surgical instrument.

5 Claims, 7 Drawing Sheets

(56) References Cited

U.S. PATENT DOCUMENTS

2013/0211531 A1    8/2013  Steines et al.
2013/0317510 A1*  11/2013  Couture ............... A61B 17/157
                                                             606/88
2014/0052136 A1    2/2014  Weber
2015/0272594 A1   10/2015  Jamali
2017/0071677 A1*   3/2017  Utz ....................... A61B 34/20

* cited by examiner

CUSTOMIZED PATIENT-SPECIFIC ORTHOPAEDIC SURGICAL INSTRUMENTS

This application is a divisional of U.S. patent application Ser. No. 15/992,059, now U.S. Pat. No. 10,856,891, which was filed on May 29, 2018, the entirety of which is hereby incorporated by reference.

TECHNICAL FIELD

The present disclosure relates generally to orthopaedic surgical instruments and, more particularly, to customized patient-specific orthopaedic surgical instruments.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint or knee prosthesis. A typical knee prosthesis includes a tibial tray, a femoral component, and a polymer insert or bearing positioned between the tibial tray and the femoral component. In a hip replacement surgical procedure, a patient's natural acetabulum is replaced by a prosthetic cup and a patient's natural femoral head is partially or totally replaced by a prosthetic stem and femoral ball.

To facilitate the replacement of the natural joint with a prosthesis, orthopaedic surgeons use a variety of orthopaedic surgical instruments such as, for example, cutting blocks, drill guides, milling guides, and other surgical instruments. Typically, the orthopaedic surgical instruments are reusable and generic with respect to the patient such that the same orthopaedic surgical instrument may be used on a number of different patients during similar orthopaedic surgical procedures.

The orthopaedic surgical instruments may also be customized to a specific patient. Such "customized patient-specific orthopaedic surgical instruments" are single-use surgical tools for use by a surgeon in performing an orthopaedic surgical procedure that is intended, and configured, for use on a particular patient. It should be appreciated that these instruments are distinct from standard, non-patient-specific orthopaedic surgical instruments that are intended for use on a variety of different patients. These customized patient-specific orthopaedic surgical instruments are distinct from orthopaedic prostheses, whether patient-specific or generic, which are surgically implanted in the body of the patient. Rather, customized patient-specific orthopaedic surgical instruments are used by an orthopaedic surgeon to assist in the implantation of orthopaedic prostheses.

SUMMARY

According to one aspect of the disclosure, an orthopaedic surgical instrument includes a first customized patient-specific surgical instrument having a body and a cutting guide slot extending through the body. The first customized patient-specific surgical instrument also includes pair of posteriorly-extending arms. Each arm includes a customized patient-specific negative contour configured to receive a portion of a corresponding positive contour of one of a patient's femoral condyles. A second customized patient-specific surgical instrument is removably coupled to the first customized patient-specific surgical instrument. The second customized patient-specific surgical instrument includes a body positioned in a gap defined between the posteriorly-extending arms. The body includes a customized patient-specific negative contour configured to receive a portion of a corresponding positive contour defining the patient's intercondylar notch.

In some embodiments, the first customized patient-specific surgical instrument may include a boss attached to, and extending from, the body to a free end spaced apart from the body. The boss may include an opening that is defined in its free end. The second customized patient-specific surgical instrument may include a boss attached to, and extending from, the body and coupled to the boss of the first customized patient-specific surgical instrument. A guide hole may extend through the boss of the first customized patient-specific surgical instrument. A guide hole may extend through the boss of the second customized patient-specific surgical instrument. The guide hole of the first customized patient-specific surgical instrument may be aligned with the guide hole of the second customized patient-specific surgical instrument.

In some embodiments, a locking mechanism may removably couple the second customized patient-specific surgical instrument to the first customized patient-specific surgical instrument. The locking mechanism may include brackets that extend distally from the body of the first customized patient-specific surgical instrument. Each bracket may have an L-shaped configuration and a catch may be defined between the bracket and a distal surface of the first customized patient-specific surgical instrument.

In some embodiments, the customized patient-specific negative contour of the first customized patient-specific surgical instrument and the customized patient-specific negative contours of the second customized patient-specific surgical instrument may form a bone-engaging surface.

In some embodiments, the first customized patient-specific surgical instrument may have a metallic guide body attached to, and extending from, the body to a free end. The guide body may have an elongated opening that is defined in its free end. The cutting guide slot may extend from the opening in the guide body and may be sized and shaped to guide a surgical tool into engagement with the patient's bone. The guide slot may be sized and shaped to guide a cutting saw blade into engagement with the patient's bone.

According to another aspect of the disclosure, an orthopaedic surgical instrument includes a cutting block having a body. A cutting guide slot extends through the body. The orthopaedic surgical instrument also includes pair of posteriorly-extending arm. Each arm includes a customized patient-specific negative contour configured to receive a portion of a corresponding positive contour of one of a patient's femoral condyles. An augment is configured to be removably coupled to the cutting block. The augment includes a body positioned in a gap defined between the posteriorly-extending arms. The body includes a customized patient-specific negative contour configured to receive a portion of a corresponding positive contour defining the patient's intercondylar notch.

In some embodiments, the cutting block may have a boss attached to, and extending from, the body to a free end spaced apart from the body. The boss may include an opening that is defined in its free end. The augment may have a boss attached to, and extending from, the body and configured to couple to the boss of the cutting block.

In some embodiments, the body of the cutting block may have a plurality of catches. The body of the augment may have a plurality of tabs. The tabs may be received in the catches to couple the augment to the cutting block. The catches may be formed in brackets that extend distally from the body of the cutting block. Each bracket may have an L-shaped configuration. The catch may be defined between the bracket and a distal surface of the cutting block.

In some embodiments, when the augment is coupled to the cutting, the customized patient-specific negative contour of the augment and the customized patient-specific negative contour of the cutting block form a bone-engaging surface.

According to yet another aspect of the disclosure, a method of resecting a distal end of a patient's femur includes advancing an orthopaedic surgical instrument assembly including a first customized patient-specific surgical instrument and a second customize patient-specific instrument into contact with a distal end of the patient's femur to position a customized patient-specific negative contour of each posteriorly-extending arm of the first customized patient-specific surgical instrument over a portion of a corresponding positive contour of one of a patient's femoral condyles and position a customized patient-specific negative contour of the second customized patient-specific surgical instrument over a portion of a corresponding positive contour defining the patient's intercondylar notch. The method also includes removing the second customized patient-specific surgical instrument from the first customized patient-specific surgical instrument so that the first customized patient-specific surgical instrument remains secured to the distal end of the patient's femur. The method also includes advancing a surgical tool through a cutting guide slot extending through the body of the first customized patient-specific surgical instrument.

In some embodiments, the method may include removing a boss attached to, and extending from, the body of the second customized patient-specific surgical instrument from a boss attached to, and extending from, the body of the first customized patient-specific surgical instrument.

In some embodiments, the method may include removing a plurality of tabs extending from the body of the second customized patient-specific surgical instrument from a plurality of catches formed in the body of the first customized patient-specific surgical instrument.

In some embodiments, the catches are formed in brackets that extend distally from the body of the first customized patient-specific surgical instrument.

In some embodiments, the method may include advancing a cutting saw blade through the cutting guide slot.

BRIEF DESCRIPTION OF THE DRAWINGS

The detailed description particularly refers to the following figures, in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Terms representing anatomical references, such as anterior, posterior, medial, lateral, superior, inferior, etcetera, may be used throughout the specification in reference to the orthopaedic implants or prostheses and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Figure 1:
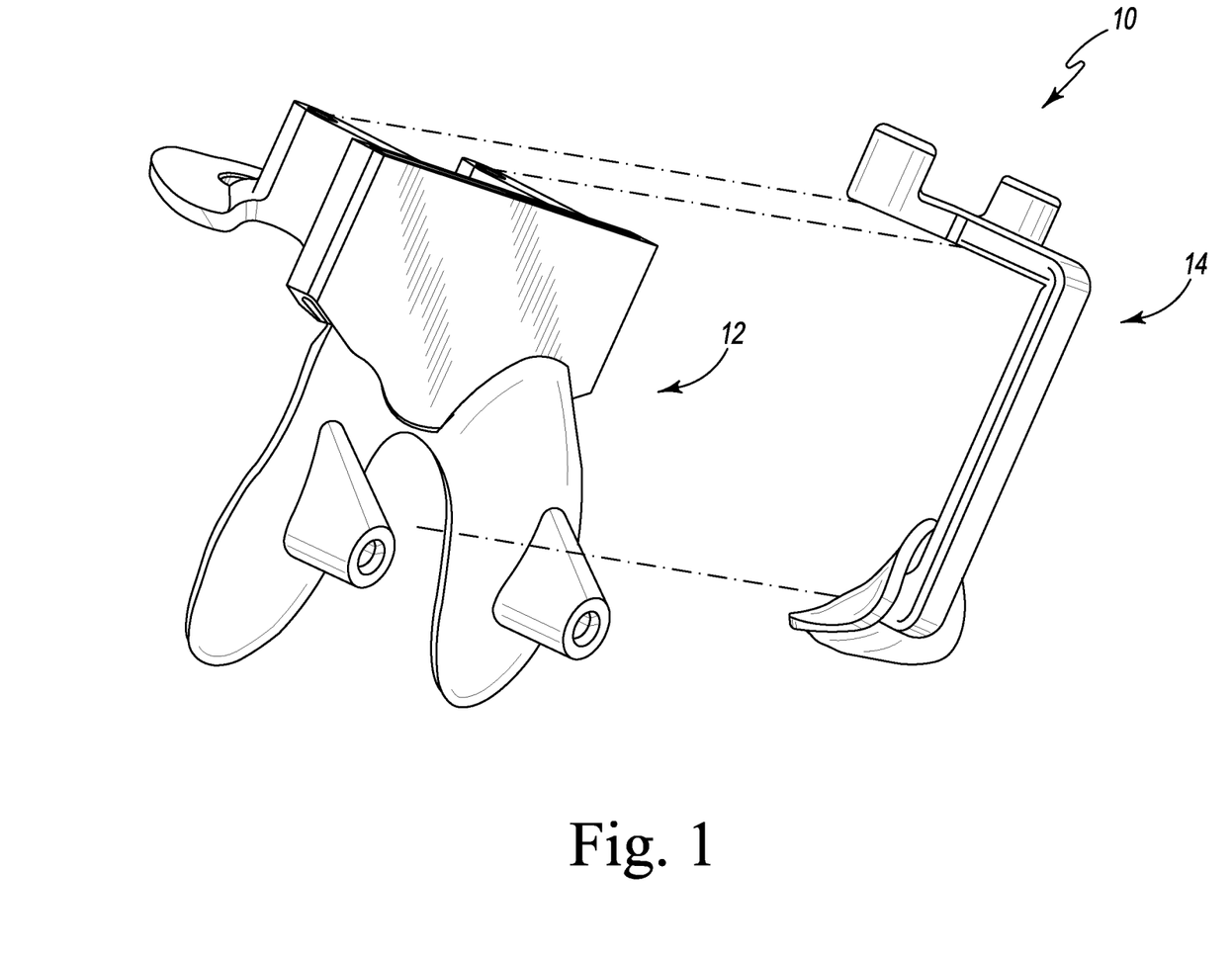
FIG. 1 is an exploded perspective view of a customized patient-specific orthopaedic surgical instrument.

Referring to FIG. 1, an orthopaedic surgical instrument 10 is shown. Instrument 10 is illustratively an assembly of two customized patient-specific orthopaedic surgical instruments. What is meant herein by the term "customized patient-specific orthopaedic surgical instrument" is a surgical tool for use by a surgeon in performing an orthopaedic surgical procedure that is intended, and configured, for use on a particular patient. As such, it should be appreciated that, as used herein, the term "customized patient-specific orthopaedic surgical instrument" is distinct from standard, non-patient-specific orthopaedic surgical instruments (i.e., "patient-universal instruments" such as patient-universal cutting blocks) that are intended for use on a variety of different patients and were not fabricated or customized to any particular patient. Additionally, it should be appreciated that, as used herein, the term "customized patient-specific orthopaedic surgical instrument" is distinct from orthopaedic prostheses or implants, whether patient-specific or generic, which are surgically implanted in the body of the patient. Rather, an orthopaedic surgeon uses customized patient-specific orthopaedic surgical instruments to assist in the implantation of orthopaedic prostheses. Examples of "customized patient-specific orthopaedic surgical instruments" include customized patient-specific drill/pin guides, customized patient-specific tibial cutting blocks, customized patient-specific femoral cutting blocks, and customized patient-specific alignment guides.

One of the customized patient-specific orthopaedic surgical instruments is a femoral cutting guide block 12. The other customized patient-specific orthopaedic surgical instrument is an augment 14 configured to be attached to the cutting block 12. The augment 14 includes a posterior contact surface that, when used in conjunction with an anterior contact surface of the cutting block 12 clamps the instrument 10 onto a distal end of the patient's femur. The posterior contact surfaces of the augment 14 along with the anterior contact surfaces of the cutting block 12 facilitate securing the cutting block 12 on the patient's femur. The augment 14 is removable from the cutting block 12 so that the instrument 10 can be disassembled and the augment 14 can be removed with the cutting block 12 in a proper position for performing a distal resection of the patient's femur. By removing the augment 14 from the cutting block 12, the augment 14 is removed from a cutting path of the surgical saw during the distal resection.

As described in greater detail below, the orthopaedic surgical instrument 10 is configured to be coupled to the patient's femur in a unique pre-determined location and orientation. Both the cutting block 12 contact region and the augment 14 contact region are configured to couple to the patient's femur in a unique pre-determined location and orientation. In the illustrative embodiment, the structure of the cutting block 12 has been contoured to reduce its size relative to conventional cutting blocks and avoid contact with undesirable regions of the patient's bone.

Figures 2, 3:
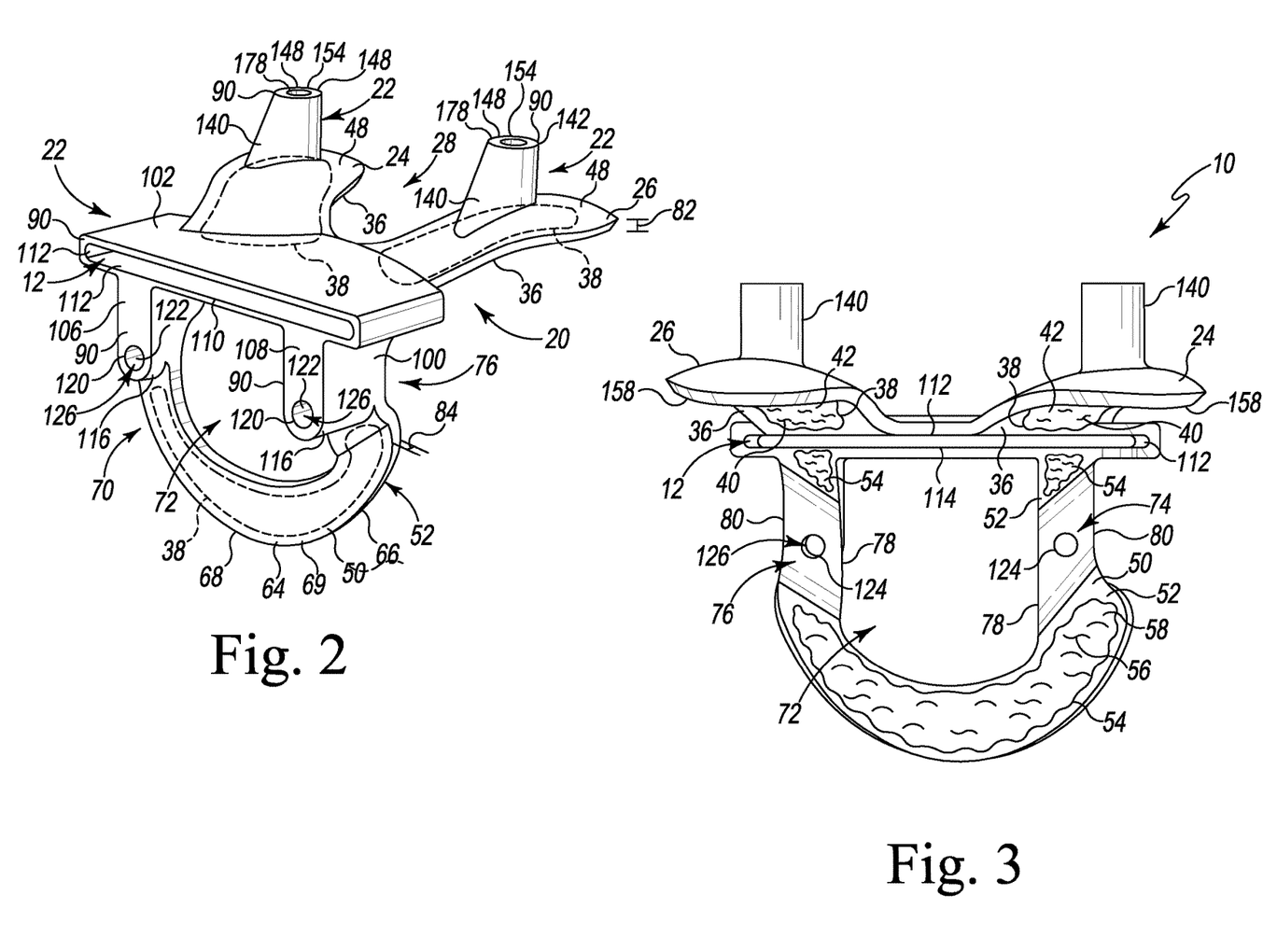
FIG. 2 is a front perspective view of the cutting block of the customized patient-specific orthopaedic surgical instrument shown in FIG. 1.
FIG. 3 is a rear elevation view of a femoral cutting guide block of the customized patient-specific orthopaedic surgical instrument shown in FIG. 1.

As shown in FIGS. 2-3, the femoral cutting block 12 includes a base plate 20 and a number of surgical tool guide bodies 22 that are attached to, and extend outwardly from, the base plate 20. In the illustrative embodiment, the femoral cutting block 12 is a single monolithic component formed from a metallic material such as, for example, stainless steel. In that way, the base plate 20 and the guide bodies 22 form a single monolithic metallic block. As described in greater detail below, the femoral cutting block 12 is formed by Direct Metal Laser Sintering (DMLS), also known as Selective Laser Sintering (SLS), which is a form of additive manufacturing technology. In DMLS, the femoral cutting block 12 is formed in a layer-by-layer fashion using laser sintering in which light fuses metallic powder, forming the metallic structures that define the femoral cutting block 12. It should be appreciated that other forms of additive manufacturing technology such as, for example, optical fabrication, photo-solidification, or resin printing may be used to fabricate the femoral cutting block 12.

Figure 6:
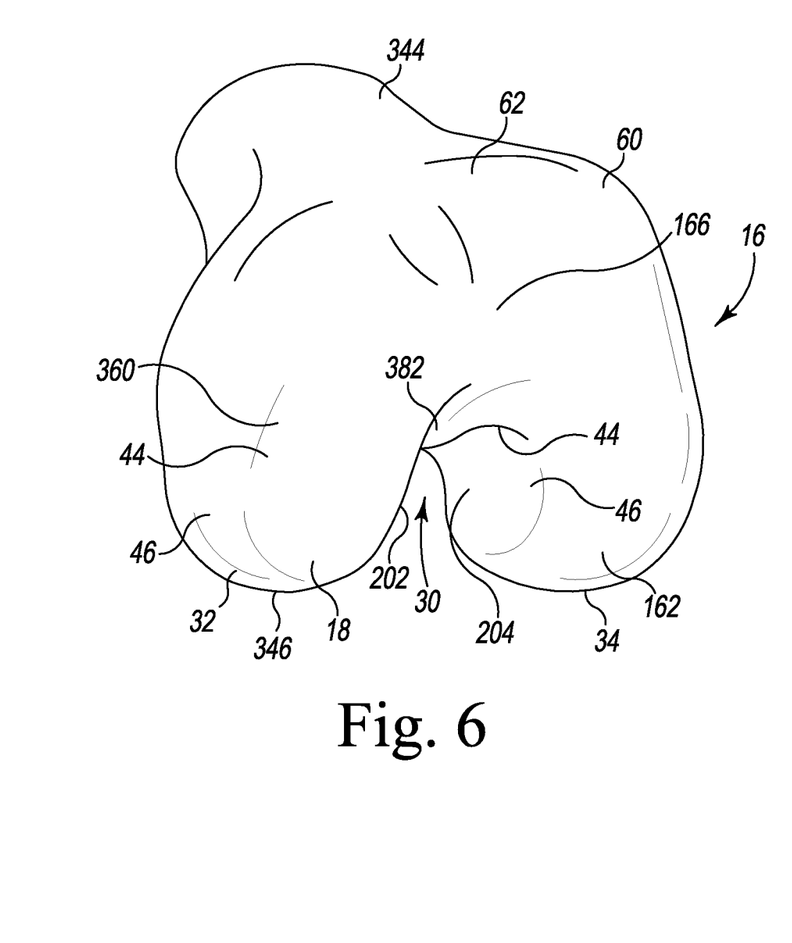
FIG. 6 is a perspective view of the distal end of a femur.

The base plate 20 includes a pair of arms 24, 26 that are configured to engage the distal end 18 of the patient's femur 16 (see FIG. 6). The arms 24, 26 are spaced apart from each other such that a notch 28 is defined between the inner edges of the arms 24, 26. The notch 28 is sized and shaped to correspond to the natural intercondylar notch 30 of the patient's femur 16, which is defined between the natural condyles 32, 34 of the patient's femur 16.

Each of the arms 24, 26 has a bone-contacting or bone-facing surface 36 that engages one of the natural condyles 32, 34. In the illustrative embodiment, each bone-facing surface 36 includes a number of negative contours 38 that are configured to receive a portion of the natural condyles 32, 34. Each contour 38 has a unique set of ridges 40 and depressions 42 that are shaped to engage a corresponding unique set of depressions 44 and ridges 46 of the natural condyles 32, 34. Each of the arms 24, 26 also includes an outer surface 48 that is positioned opposite its corresponding bone-facing surface 36. In the illustrative embodiment, each outer surface 48 is substantially smooth. As used herein, the term "substantially" should be understood to refer to the normal tolerances created by manufacturing variation and other design criteria. As such, a "substantially smooth surface" is one that is smooth within the normal tolerances created or permitted by manufacturing variation and other design criteria.

The base plate 20 also includes an anterior flange 50 that is configured to engage the distal end 18 of the patient's femur 16. The anterior flange 50 includes a bone-facing surface 52 that includes a number of negative contours 54 that are configured to receive a portion of the patient's femur 16. The contour 54 of the anterior flange 50 has a unique set of ridges 56 and depressions 58 that are shaped to engage a corresponding unique set of depressions 60 and ridges 62 of the patient's femur 16. The anterior flange 50 also includes an outer surface 64 that is positioned opposite the bone-facing surface 52. In the illustrative embodiment, the outer surface 64 is substantially smooth.

The negative contours 38, 54 of the base plate 20 permit the cutting block 12 (and hence the tool guide bodies) to be positioned on the patient's femur 16 in a unique pre-determined location and orientation. The bone-facing surface 52 includes a pair of curved posterior edges 66, 68 that define a portion of the contour 54 and are shaped to match a portion of the patient's femur. As a result, each of the edges 66, 68 includes convex and concave portions to receive corresponding concave and convex portions of the patient's femur 16. The edge 66 includes a posterior tip 69 that is sized and shaped to be positioned in the patient's natural trochlear groove 166.

The base plate 20 also includes a number of customized cavities 70, which are sized to be positioned over regions in the pre-determined location of the bone that may include a defect or are damaged or difficult to model. In that way, the cavities 70 are sized such that contact with those regions may be avoided so as to not interfere with positioning the cutting block 12 in the pre-determined location and orientation. In the illustrative embodiment, the notch 28 defined between the arms 24, 26 is one of the customized cavities. The customized cavities 70 also include an aperture 72 that extends through the bone-facing surface 52 of the anterior flange 50. The customized cavities 70 also include a pair of channels 74, 76 that are defined in the bone-facing surface 52 of the anterior flange 50. In the illustrative embodiment, each channel 74, 76 extends from an end 78 that opens into the aperture 72 to an open end 80 that is defined in the outer edge of the anterior flange 50.

In the illustrative embodiment, the base plate 20 of the cutting block 12 has a low-profile to reduce the size of the incision and reduce the amount of bone displacement needed to position the cutting block 12. The low-profile has been customized for block 12 by minimizing the thicknesses of the arms 24, 26 and the anterior flange 50. A thickness 82 is defined between the outer surface 48 and the bone-facing surface 36 of each arm. To minimize the thickness 82, the outer surface 48 of each arm is convexly curved to follow the concave curvature of the bone-facing surface 36. Similarly, a thickness 84 is defined between the outer surface 64 and the bone-facing surface 52 of the anterior flange 50, and the outer surface 64 of the flange 50 is shaped to follow the geometry of the bone-facing surface 52 to minimize the thickness 84.

Each of the surgical tool guide bodies 22 of the cutting block 12 is attached to and extends outwardly from the outer surfaces 48, 64 of the arms 24, 26 and the anterior flange 50 to a free end 90 that is spaced apart from the base plate 20. In the illustrative embodiment, the guide bodies 22 include an anterior guide body 100 that extends anteriorly from the anterior ends of the arms 24, 26 and the anterior flange 50 to its free end 102. The anterior guide body 100 includes a distal flange 104 and a pair of bosses 106, 108 that extend proximally from the flange 104. As shown in FIG. 1, the aperture 72 defined in the base plate 20 is positioned proximal of the distal flange 104 and between the bosses 106, 108.

The distal flange 104 of the anterior guide body 100 includes an elongated opening 110 that is defined in the free end 102 and a number of inner walls 112 that extend inwardly from the opening 110. As shown in FIG. 2, the inner walls 112 extend to another opening 114 that is defined in the bone-facing surface 52. The opening 114 extends through the contour 54 of the base plate 20 such that the opening 114 is defined by the edges 66, 68 of the bone-facing surface 52, which follow a curved, irregular path that matches the shape of the patient's femur 16 in that region. The opening 114 cooperates with the inner walls 112 and the elongated opening 110 to define the guide slot 98, which is sized and shaped to guide a surgical tool such as, for example, a cutting blade, into engagement with the patient's bone. As described above, the cutting guide slot 98 is positioned to guide a customized, patient-specific resection of the distal end 18 of the patient's femur 16. Because the edge 66 follows the shape of the patient's femur 16 and the posterior tip of the edge 66 extends into the patient's trochlear groove, the cutting guide slot 98 provides support for the cutting blade in close proximity to the region under resection.

As shown in FIG. 2, each of the bosses 106, 108 extend from a proximal surface 116 of the distal flange 104 to a curved proximal end 116. It should be appreciated that in other embodiments one or both of the bosses 106, 108 may be spaced apart from the distal flange 104, thereby forming separate guide bodies. An opening 120 is defined in the free end 102 of each of the bosses 106, 108 adjacent to the proximal end 118. An inner wall 122 extends inwardly from the opening 120. As shown in FIG. 3, each inner wall 122 extends to another opening 124 that opens into one of the channels 74, 76 to define a guide slot 126 extending through the cutting block 12. In the illustrative embodiment, each guide slot 126 is a drill guide and fixation pin guide hole, which is sized and shaped to guide a surgical drill to prepare the patient's bone to receive a fixation pin to couple the block 12 to the bone.

The guide bodies 22 include a pair of posterior guide bosses 140, which are attached to, and extend distally from, the outer surfaces 48 of the arms 24, 26, respectively. Each posterior guide boss 140 includes a guide slot 142 that is sized and shaped to guide a surgical drill and a fixation pin into engagement with the patient's bone to couple the block 12 to the bone. Each guide boss 140 includes a post 144 that extends from a base 146 attached to the outer surface 48 of one of the arms 24, 26 to a free end 148 that is spaced apart from the outer surface 48.

An opening 154 is defined in the free end 148 of each boss 140. An inner wall 178 extends inwardly from the opening 154 to another opening 158 that is defined in a bone-facing surface 36 of one of the arms 24, 26. The openings 154, 158 and the inner wall 178 cooperate to define the guide slot 142. As described above, each guide slot 142 is a drill guide and fixation pin guide hole, which is sized and shaped to guide a surgical drill or self-drilling fixation pin to prepare the patient's bone to receive a fixation pin to couple to the block 12 to the bone.

Figure 4:
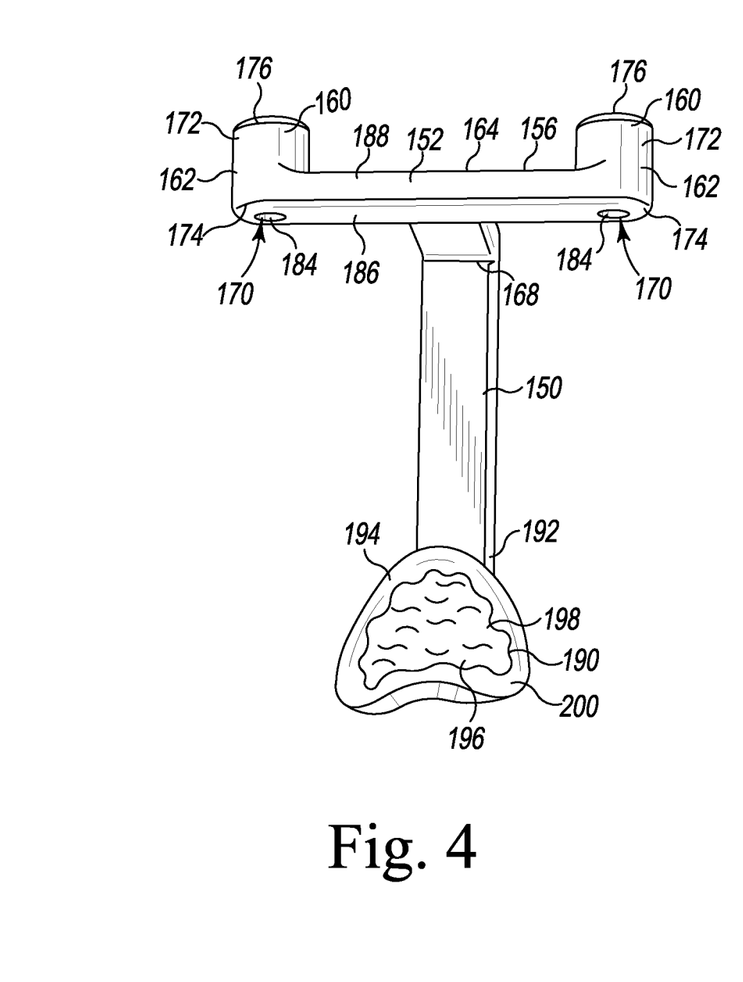
FIG. 4 is a rear perspective view of an augment of the customized patient-specific orthopaedic surgical instrument shown in FIG. 1.
Figure 5:
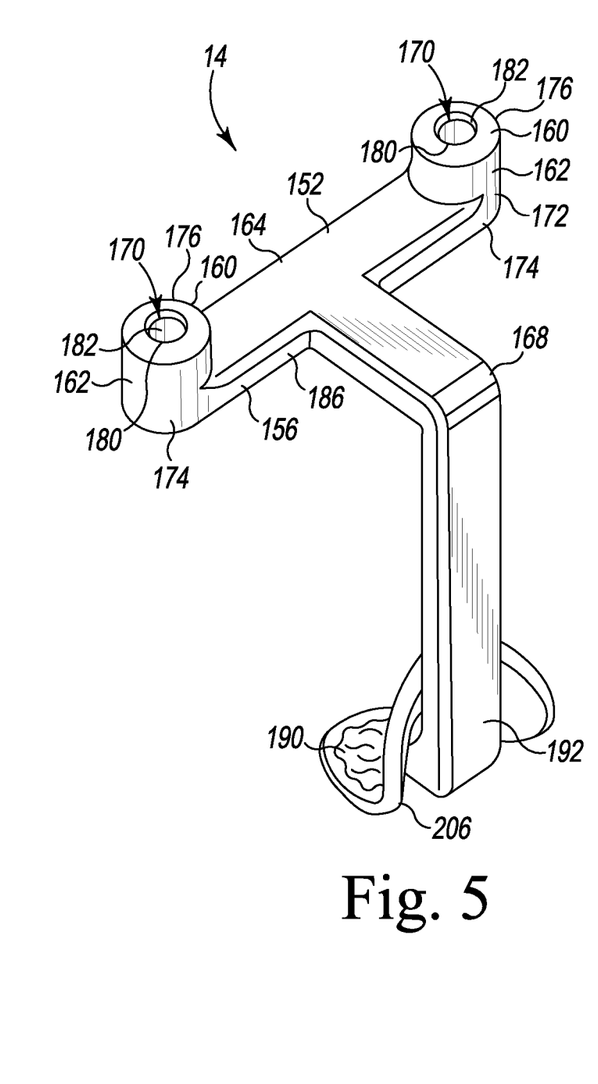
FIG. 5 is a front perspective view of the augment of the customized patient-specific orthopaedic surgical instrument shown in FIG. 1.

As described above, the instrument 10 also includes an augment 14 configured to be attached to the cutting block 12. The augment 14 is configured to lock the cutting block 12 into position on the bone and prevent rotation of the cutting block 12. Referring now to FIGS. 4-5, the augment 14 includes an elongated body 150. An anterior flange 152 extends proximally from an anterior end 168 of the body 150 and includes a medial arm 156 and a lateral arm 188. A guide body 160 extends from each of the medial arm 156 and the lateral arm 188. The guide bodies 160 include a pair of guide bosses 162, which are attached to, and extend anteriorly from, the outer surfaces 164 of the arms 156, 158, respectively. Each guide boss 162 includes a guide slot 170 that is sized and shaped to guide surgical drill and/or a fixation pin into engagement with the patient's bone to couple to the augment 14 through the cutting block 12 to the bone. Each guide boss 162 includes a post 172 that extends from a base 174 attached to the outer surface 164 of one of the arms 156, 158 to a free end 176 that is spaced apart from the outer surface 164.

An opening 180 is defined in the free end 176 of each boss 162. An inner wall 182 extends inwardly from the opening 180 to another opening 184 that is defined in a posterior surface 186 of one of the arms 156, 158. The openings 180, 184 and the inner wall 182 cooperate to define the guide slot 170. As described above, each guide slot 170 is a drill guide and fixation pin guide hole, which is sized and shaped to guide a surgical drill or self-drilling fixation pin to prepare the patient's bone to receive a fixation pin to couple the augment 14 to the bone. The bosses 162 are coupled to the bosses 106, 108 of the cutting block 12. In some embodiments, the bosses 162 and the bosses 106, 108 include a fastening mechanism to couple the bosses 162 to the bosses 106, 108. For example, the bosses 162 may include peg features that are received in openings on the bosses 106, 108 to secure the augment 14 to the cutting block 12. In some embodiments, the pegs are provided on the bosses 106, 108 and the openings to receive the pegs are provided on the bosses 162. It will be appreciated that other fastening mechanisms may be utilized to secure the bosses 162 to the bosses 106, 108. The guide slots 170 of the augment 14 are aligned with the guide slots 126 of the cutting block 12. The fixation pins are inserted into the guide slots 170 and advanced through the guide slots 126 to secure the instrument 10 to the patient's femur.

The elongated body 150 is customized patient-specific. A space between the bosses 162 and a position of the bosses 162 relative to the elongated body 150 is customized to position the bosses 162 over the bosses 106, 108. The elongated body 150 of the augment 14 may be angled to customize the elongated body 150 to a size and shaped of the distal end of the patient's femur. The elongated body 150 is sized and shaped relative to a size and shape of the patient's intercondylar notch 30.

A patient-specific block 190 extends from a posterior end 192 of the elongated body 150. The block 190 is configured to extend into the intercondylar notch 30 of the patient's femur 16 and engage a surface that defines the intercondylar notch 30. The elongated body 150 is sized, shaped, and angled relative to the anterior flange 152 and the block 190 so that the block 190 engages the surface defining the intercondylar notch 30. The block 190 includes a convex shape that enables the body to position within the intercondylar notch 30 and engage a surface 382 defining the intercondylar notch 30. The block 190 includes a bone-facing surface 194 that includes a number of negative contours 196 that are configured to receive a portion of the surface 382 defining the patient's intercondylar notch 30. The contour 196 of the block 190 has a unique set of ridges 198 and depressions 200 that are shaped to engage a corresponding unique set of depressions 202 and ridges 204 of a positive contour defining the patient's intercondylar notch 30. The block 190 also includes an outer surface 206 that is positioned opposite the bone-facing surface 194. In the illustrative embodiment, the outer surface 206 is substantially smooth.

Referring now to FIG. 6, the patient's femur 16 includes the distal end 18 having a pair of condyles 32, 34 extending between an anterior surface 344 and a posterior surface 346. The anterior surface 344 includes a plurality of ridges 62 and depressions 60 that define a patient-specific positive contour of the anterior surface 344. The condyles 32, 34 include a medial condyle 32 and a lateral condyle 34. The medial condyle 32 and the lateral condyle 34 include condylar surfaces 360 having ridges 46 and depressions 44 that define a positive patient-specific contour of the condyles 32, 34. The intercondylar notch 30 extends between the medial condyle 32 and the lateral condyle 34. The intercondylar notch 30 is defined by the surface 382 which has a plurality of ridges 204 and depressions 202 that define a positive patient-specific contour of the surface 382.

Figure 7:
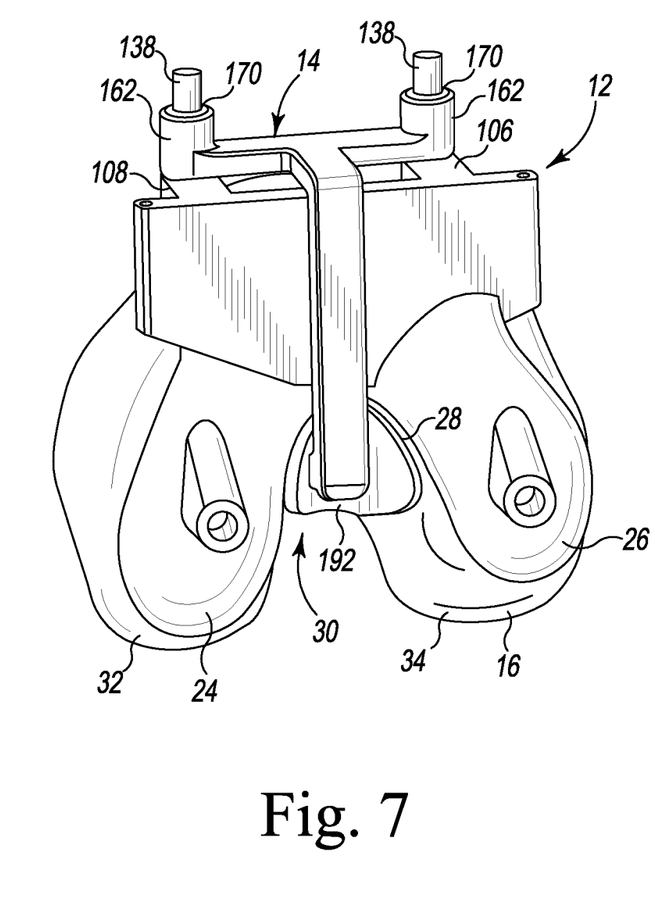
FIG. 7 is a perspective view of the customized patient-specific orthopaedic surgical instrument shown in FIG. 1 positioned on the distal end of the femur.

Referring to FIG. 7, in use, the augment 14 is coupled to the cutting block 12 by the fastening mechanism on the bosses 162 and the bosses 106, 108. The guide slots 142 of the cutting block 12 are aligned with the guide slots 170 of the augment 14. In some embodiments, the cutting block 12 and the augment 14 are coupled during surgery. In some embodiments, the cutting block 12 and the augment 14 are coupled together during manufacturing. The surgeon positions the cutting block 12 on the distal end of the patient's femur 16 so that the bone-facing surface 52 of the anterior flange 50 is positioned on the anterior surface 344 of the femur 16 and the ridges 56 and depressions 58 engage the depressions 60 and ridges 62, respectively, of the anterior surface 344. The bone-facing surfaces 36 of the arm 24 engage the natural condyle 32 of the patient's femur 16 so that the ridges 40 and depressions 42 of the arm 24 engage the depressions 44 and ridges 46, respectively, of the condyle 32. The bone-facing surfaces 36 of the arm 26 engage the natural condyle 34 of the patient's femur 16 so that the ridges 40 and depressions 42 of the arm 26 engage the depressions 44 and ridges 46, respectively, of the condyle 34. The body 192 of the augment 14 is positioned within the notch 28 defined between the inner edges of the arms 24, 26 of the cutting block. The bone-facing surface 194 of the body 192 engages the surface 382 defining the intercondylar notch 30 of the femur 16 so that the ridges 198 and depressions 200 engage the depressions 202 and ridges 204, respectively, of the surface 382. The block 190 is positioned within the notch 28 so that the bone-facing surfaces 36 and the bone-facing surface 194 form a bone-facing surface that includes a patient-specific negative contour configured to match and receive the positive contour of the distal end 18 of the femur 16.

The surgeon couples the instrument 10 to the femur 16 by advancing the fixation pins 138 extending through the guide slots 170, 142 into the bone. The surgeon further couples the cutting block 12 to the femur 16 by advancing the fixation pins in the guide slots 126 into the bone. In some embodiments, the surgeon drills openings into the bone to receive the fixation pins. The openings may be drilled by inserting a drill through the guide slots. With the instrument 10 in place, the augment 14 is removed by sliding the bosses 162 along the fixation pins to decouple the augment 14 from the patient's bone. When the augment 14 is removed, a distal resection of the femur is performed by advancing a surgical cutting blade through the guide slot 98.

Figure 8:
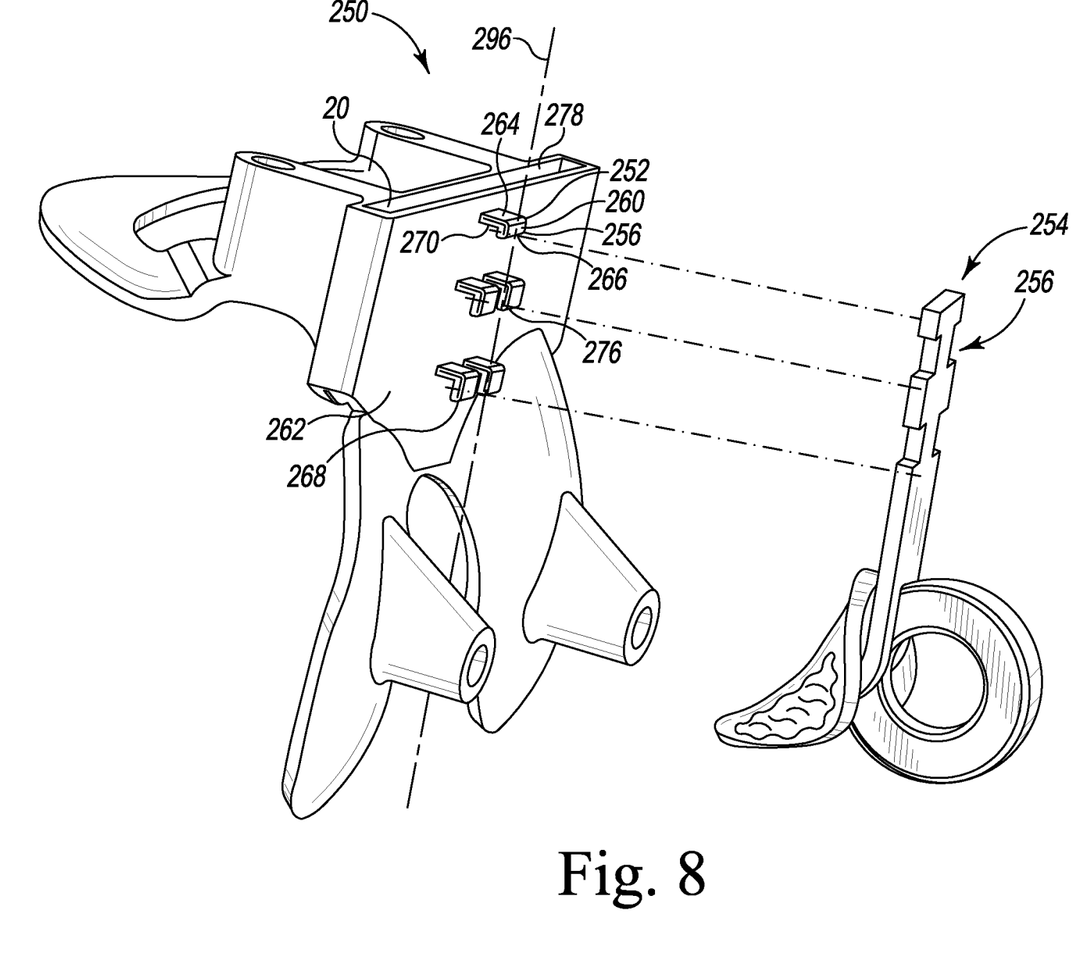
FIG. 8 is an exploded perspective view of another customized patient-specific orthopaedic surgical instrument.

Referring to FIG. 8, another customized patient-specific orthopaedic surgical instrument 250 includes a cutting block 252 and an augment 254. Structures of the cutting block 252 that are the same as the structures of the cutting block 12 are referred to using the same references numbers.

The cutting block 252 includes a locking mechanism 256 having a plurality of brackets 260 extending from a distal surface 262 of the base plate 20. Each bracket 260 has an L-shaped configuration including an anterior flange 264 extending distally from the base plate 20. A distal flange 266 extends posteriorly from the anterior flange 264. The flanges 264, 266 and the distal surface 262 of the base plate 20 define a locking catch 270 on the base plate 20. An opening 272 extends between an end 274 of each distal flange 266 and the distal surface 262. The catch 270 extends from the opening 272 to the anterior flange 264. In the illustrative embodiment, the cutting block 252 includes five brackets 260 defining five catches 270. In other embodiments, the cutting block 252 may include any number of brackets 260. A pair of posterior brackets 268 is positioned posteriorly of a pair of intermediate brackets 276, and an anterior bracket 278 is positioned anteriorly of the pair of intermediate brackets 276. The pair of posterior brackets 268 and the pair of intermediate brackets 276 are spaced apart from a centerline 296 of the base plate 20. The anterior bracket 278 is aligned with the centerline 296.

Figure 9:
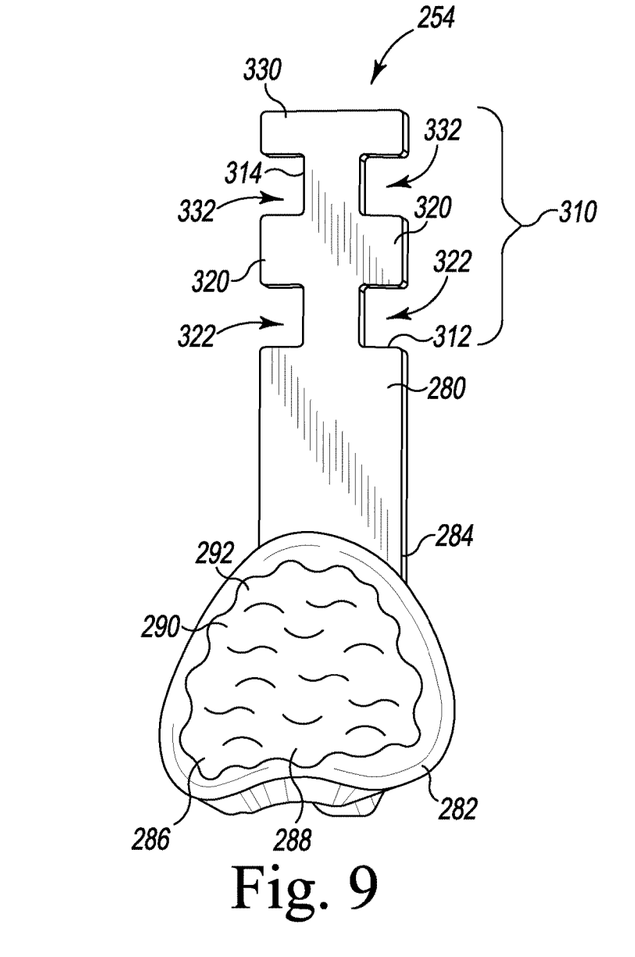
FIG. 9 is a rear perspective view of an augment of the customized patient-specific orthopaedic surgical instrument shown in FIG. 8.
Figure 10:
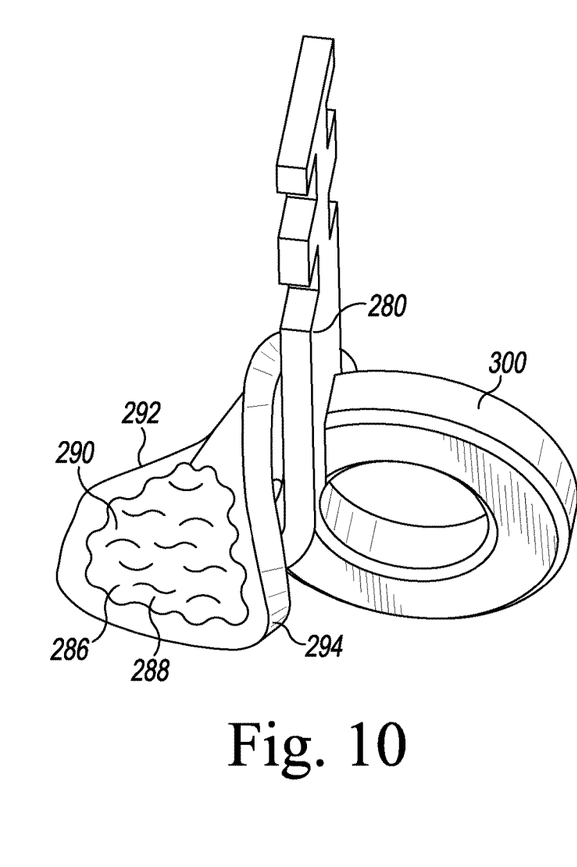
FIG. 10 is a side perspective view of the augment of the customized patient-specific orthopaedic surgical instrument shown in FIG. 8.

Referring to FIGS. 9-10, the augment 254 includes an elongated body 280. A patient-specific block 282 extends from a posterior end 284 of the elongated body 280. The block 282 is configured to engage the intercondylar notch 30 of the patient's femur 16. The block 282 includes a convex shape that enables the body to position within the intercondylar notch 30 and engage a surface of the intercondylar notch 30. The block 282 includes a bone-facing surface 286 that includes a number of negative contours 288 that are configured to receive a portion of the surface 382 defining the patient's intercondylar notch 30. The contour 288 of the block 282 has a unique set of ridges 290 and depressions 292 that are shaped to engage a corresponding unique set of depressions 202 and ridges 204 of the surface 382 defining the patient's intercondylar notch 30. The block 282 also includes an outer surface 294 that is positioned opposite the bone-facing surface 286. In the illustrative embodiment, the outer surface 294 is substantially smooth. A handle 300 extends distally from the outer surface 294. The handle 300 is rounded in a ring configuration; however, the handle may take any desirable shape.

A locking flange 310 extends from an anterior end 312 of the elongated body 280. The locking flange 310 includes a main body 314 extending from the anterior end 312. Intermediate tabs 320 extend medially and laterally from the main body 314. A pair of intermediate notches 322 is defined by the main body 314, the intermediate tabs 320, and the anterior end 312 of the elongated body 280. An end tab 330 extends medially and laterally from the main body 314 anteriorly of the intermediate tabs 320. A pair of end notches 332 is defined by the main body 314, the intermediate tabs 320, and the end tab 330.

Figure 11:
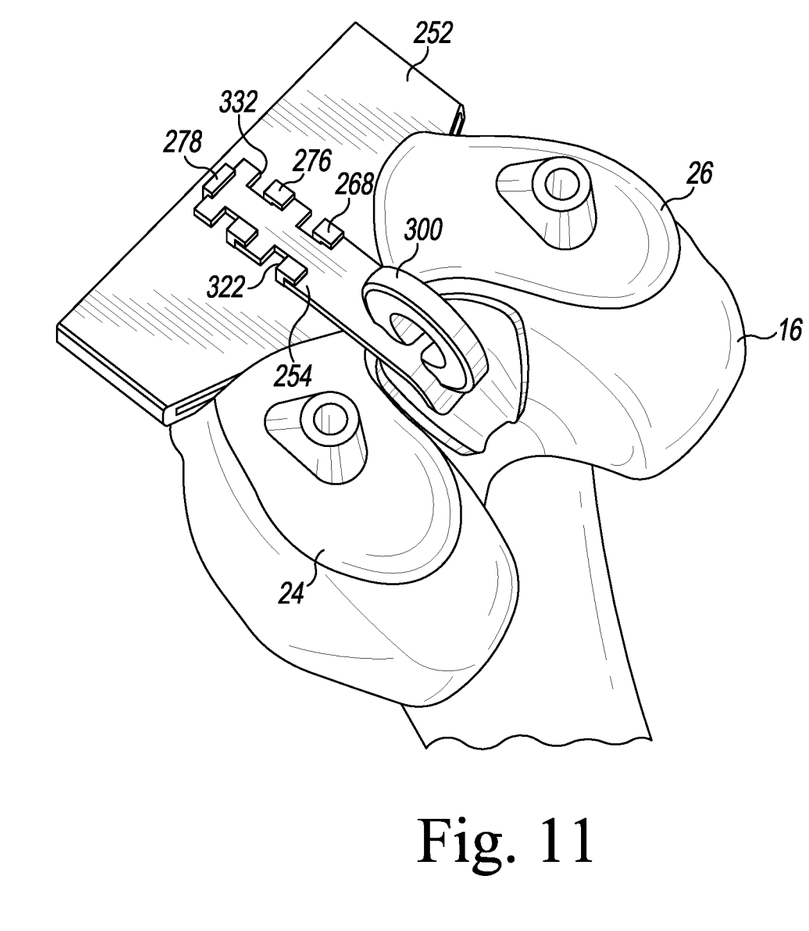
FIG. 11 is front perspective view of the customized patient-specific orthopaedic surgical instrument shown in FIG. 8 positioned on the distal end of the femur.

Referring to FIG. 11, the augment 254 is aligned with the cutting block 252 so that the posterior brackets 268 of the cutting block 252 are inserted into the intermediate notches 322 of the augment 254 and the intermediate brackets 276 of the cutting block 252 are inserted into the end notches 332 of the augment 254. The augment 254 is advanced anteriorly so that the anterior end 312 of the elongated body 280 is received in the catches 270 defined by the pair of posterior brackets 268. The intermediate tabs 320 of the augment 254 are advanced into the catches 270 defined by the pair of pair of intermediate brackets 276. Also, the end tab 330 is advanced into the catch 270 defined by the anterior bracket 278. In some embodiments, the augment 254 is coupled to the cutting block 252 during surgery. In some embodiments, the augment 254 is coupled the cutting block 252 during manufacturing.

The surgeon positions the cutting block 252 on the distal end of the patient's femur 16 so that the bone-facing surface 52 of the anterior flange 50 is positioned on the anterior surface 344 of the femur 16 and the ridges 56 and depressions 58 engage the depressions 60 and ridges 62, respectively, of the anterior surface 344. The bone-facing surfaces 36 of the arm 24 engage the natural condyle 32 of the patient's femur 16 so that the ridges 40 and depressions 42 of the arm 24 engage the depressions 44 and ridges 46, respectively, of the condyle 32. The bone-facing surfaces 36 of the arm 26 engage the natural condyle 34 of the patient's femur 16 so that the ridges 40 and depressions 42 of the arm 26 engage the depressions 44 and ridges 46, respectively, of the condyle 34. The block 282 of the augment 254 is positioned within the notch 28 defined between the inner edges of the arms 24, 26 of the cutting block. The bone-facing surface 286 of the block 282 engages the surface 382 of defining the intercondylar notch 30 of the femur 16 so that the ridges 290 and depressions 292 engage the depressions 202 and ridges 204, respectively, of the surface 382. The block 282 is positioned within the notch 28 so that the bone-facing surfaces 36 and the bone-facing surface 286 form a bone-facing surface that is a patient-specific negative contour configured to match the contour of the distal end 18 of the femur 16.

The surgeon couples the instrument 10 to the femur 16 by advancing the fixation pins through the guide slots 170, 142 and into the bone. The surgeon further couples the cutting block 12 to the femur 16 by advancing the fixation pins through the guide slots 126 and into the bone. In some embodiments, the surgeon drills openings into the bone to receive the fixation pins. The openings may be drilled by inserting a drill through the guide slots. With the instrument 10 in place, the augment 254 is removed by advancing the augment 14 posteriorly and a distal resection of the femur is performed by advancing a surgical cutting blade through the guide slot 98.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It should be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A method of resecting a distal end of a patient's femur comprising:
   advancing an orthopaedic surgical instrument assembly including a first customized patient-specific surgical instrument and a second customized patient-specific surgical instrument into contact with a distal end of the patient's femur to position a customized patient-specific negative contour of each posteriorly-extending arm of the first customized patient-specific surgical instrument over a portion of a corresponding positive contour of one of a patient's femoral condyles and position a customized patient-specific negative contour of the second customized patient-specific surgical instrument over a portion of a corresponding positive contour defining the patient's intercondylar notch,
   removing the second customized patient-specific surgical instrument from the first customized patient-specific surgical instrument so that the first customized patient-specific surgical instrument remains secured to the distal end of the patient's femur, and
   advancing a surgical tool through a cutting guide slot extending through a body of the first customized patient-specific surgical instrument.

2. The method of claim 1, wherein removing the second customized patient-specific surgical instrument further comprises removing a boss attached to, and extending from, a body of the second customized patient-specific surgical instrument from a boss attached to, and extending from, the body of the first customized patient-specific surgical instrument.

3. The method of claim 1, wherein removing the second customized patient-specific surgical instrument further comprises removing a plurality of tabs extending from a body of the second customized patient-specific surgical instrument from a plurality of catches formed in the body of the first customized patient-specific surgical instrument.

4. The method of claim 3, wherein the catches are formed in brackets that extend distally from the body of the first customized patient-specific surgical instrument.

5. The method of claim 1, further comprising advancing a cutting saw blade through the cutting guide slot.

* * * * *